United States Patent [19]

van Amerongen

[11] E Re. 30,046

[45] Reissued Jul. 17, 1979

[54] NEBULIZER

[75] Inventor: Edward van Amerongen, Wilmette, Ill.

[73] Assignee: Respiratory Care, Inc., Arlington Heights, Ill.

[21] Appl. No.: 553,081

[22] Filed: Feb. 26, 1975

Related U.S. Patent Documents

Reissue of:

[64] Patent No.: 3,771,721
Issued: Nov. 13, 1973
Appl. No.: 286,692
Filed: Sep. 6, 1972

[51] Int. Cl.[2] ..... A61M 11/02

[52] U.S. Cl. ..... 239/338; 128/194

[58] Field of Search ..... 239/338, 343, 309, 124, 239/120, 370, 433; 128/194

[56] References Cited

U.S. PATENT DOCUMENTS

| | | | |
|---|---|---|---|
| 2,605,764 | 8/1952 | Adams | 128/194 X |
| 3,525,476 | 8/1970 | Boling | 239/338 |
| 3,652,015 | 3/1972 | Beall | 239/338 |

*Primary Examiner*—Richard A. Schacher
*Attorney, Agent, or Firm*—Eric P. Schellin

[57] ABSTRACT

A water supply is adapted as a source for nebulized liquid through the agency of an adapter which couples oxygen pressure to a container for the water. A venturi within the adapter draws from the water supply and directs highly atomized water and oxygen through an outlet pipe on the adapter. The adapter is also provided with means of providing air to the outgoing stream in order to dilute the oxygen content.

A depending suspended ball is disposed in the path of flow downstream of the venturi in a chamber. It traps water particles which should not pass to the patient. The water particles or drops collected in the chamber are drained into a means located at the bottom of the chamber. Means is located along and at the bottom to assist in collecting the liquid water and conducting it to the drain means. Conduit means is fluidally connected to the drain means and to the container for both carrying back the collected liquid water and for stabilizing pressure in the container by providing gas replacement for water removed from the system.

10 Claims, 9 Drawing Figures

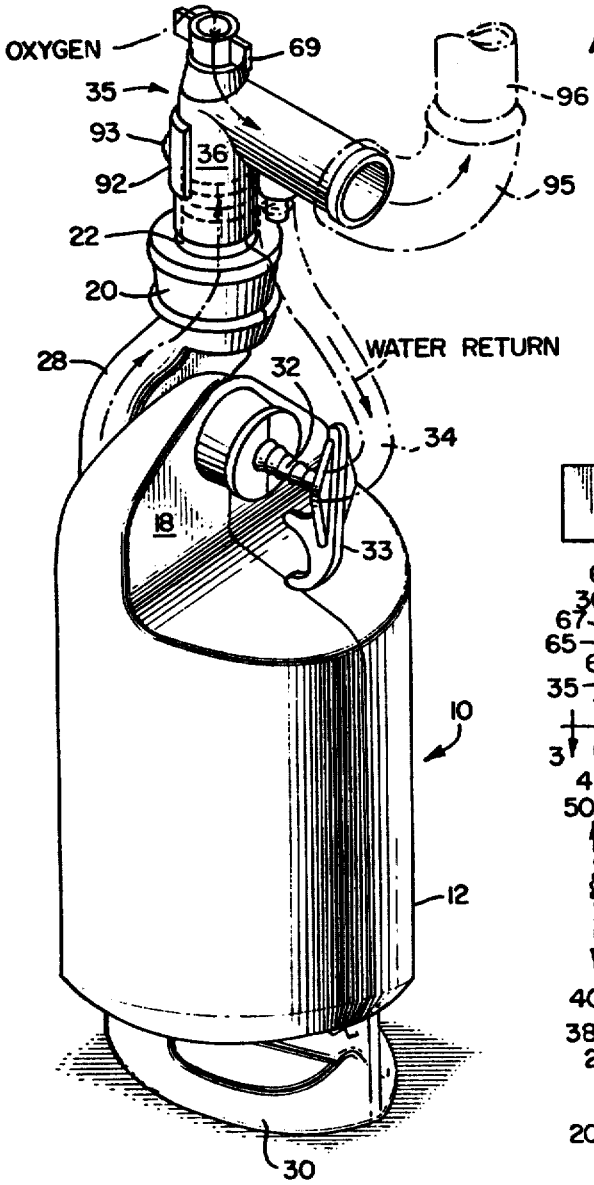
FIG. 1.
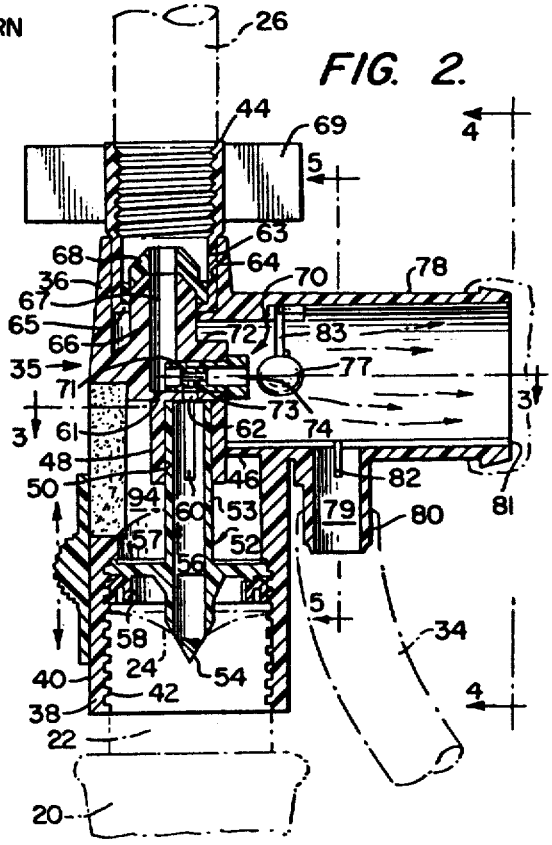
FIG. 2.
FIG. 3.
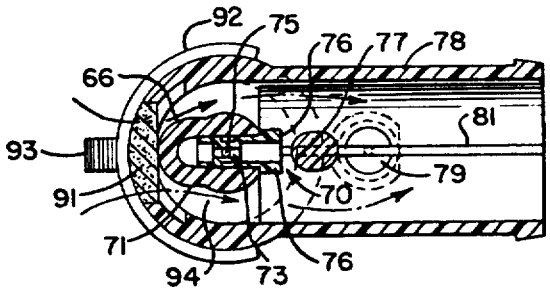

NEBULIZER

Matter enclosed in heavy brackets [ ] appears in the original patent but forms no part of this reissue specification; matter printed in italics indicates the additions made by reissue.

FIELD OF THE INVENTION

The present disclosure relates to inhalation therapy. Particularly it relates to nebulizers. Specifically it concerns a nebulizer adapter for a liquid container.

BACKGROUND OF THE INVENTION

Inhalation therapy is the medical art of treating with oxygen or a mixture of oxygen and air having a high moisture content. Several classes of devices, one of which comprises atomizers or nebulizers, are adapted for effecting such treatments. A heretofore known system for inhalation thereby comprises a container for pure water which has means enabling operation of the container in one of several modes. A fitting, comprised of a venturi, when associated with said enabling means, adapts the container as a nebulizer reservoir and itself is adapted for providing nebulized water. However, in that device, some of the water which has been removed from the container either fails to break into a mist, or condenses at or about the fitting after atomization.

The patentee in the recently issued U.S. Pat. No. 3,652,015, goes a long way to solving some of the basic problems in this area. The present invention constituting the subject matter herein provides for an improved means for disposing of the unatomized water. It also provides for a more expeditious construction. It also provides for better mode of securing the parts of the device to connecting conduits and to the container constituting the nebulizer reservoir.

Accordingly, it is an object of the invention to provide an improved nebulizer.

It is a further object of the invention to provide an improved fitting for adapting a water container as a nebulizer.

It is another object of the invention to remove condensate from a mist produced by a nebulizer, particularly a nebulizer comprised of a venturi.

It is an additional object of the invention to improve the quality of a nebulized mist.

Further, it is an object of the invention to improve the fitting arrangements of the nebulizer device.

Moreover, it is an object of the invention to easily return condensate in a nebulizer to its associated reservoir.

SUMMARY OF THE INVENTION

To effect the foregoing, and other objects of the invention which will be apparent from the ensuing description, a nebulizer, has a venturi for mist forming means disposed within a body having chamber means with a mist outlet opening. Provided are means for removing from said body a stream of fluid collected in said chamber means. More particularly, the nebulizer has a delivering pipe disposed in fluid receiving association with said venturi. A wall section of said pipe has a ridge portion arranged for coalescing and draining said chamber means; and an opening in said wall is adapted to drain said chamber means.

BRIEF DESCRIPTION OF THE DRAWINGS

In the ensuing description, reference is made to the accompanying drawings in which:

FIG. 1 is a perspective of the device of the present invention mounted on a reservoir containing water.

FIG. 2 is a vertical sectional view through a nebulizer embodying the inventive, only an upper portion of an associated container with a nebulizer adapter being shown.

FIG. 3 is a cross-sectional view taken along line 3—3 of FIG. 2.

DETAILED DESCRIPTION OF THE ILLUSTRATED EMBODIMENT

Figure 4:
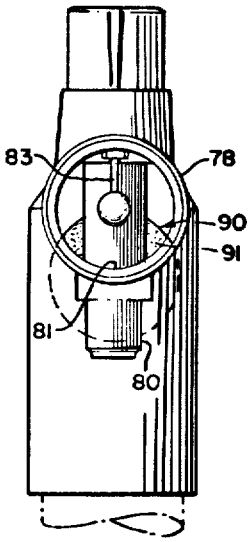
FIG. 4 is a front elevational view of the device of the present invention.
Figure 5:
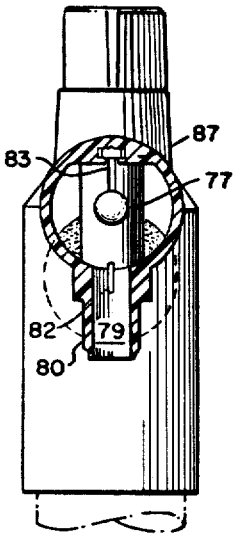
FIG. 5 is a cross-sectional view taken along line 5—5 of FIG. 2.

Referring now more particularly to the drawings, shown is a container generally designated 10, which may be of semirigid fabrication and has a general vertical orientation. It is comprised of a body 12 having therein a chamber which defines a reservoir for water. A neck 18, being an upper restricted end portion of body 12 serves as a transition component atop of which is fashioned an integral head 20. Inlet means comprised of a duct 22 is integrally fashioned with 20 and extends vertically upwardly, its inlet end portion having mounted therein a flexible sealing disc, membrane or diaphragm 24 which is shown ruptured for fluidally connecting the container with an oxygen supply source 26.

A septum (not shown) is formed integrally with and is disposed within the body 12, with the wall of said body, defines a duct 28 with a generally vertical aspect. The septum separates the chamber, being primarily the reservoir, from duct 28; but at its lower end 30 terminates short of the container bottom, whereat the chamber and the duct are fluidally connected. The upper portion of the septum extends obliquely across the chamber. The neck 18 being fashioned such that a path for gas is formed between the duct 22 and the duct 28.

The foregoing construction enables use of container 10 as a humidifier reservoir (such use not being illustrated herein) as well as nebulizer reservoir, as illustrated herein. This dual feature is disclosed and described in detail in a copending application, Ser. No. 856,756, filed Sept. 10, 1969.

A liquid return nipple 32 is fashioned integrally with neck 18 and preferably is disposed above the highest level in the chamber. In addition, nipple 32 comprises venting means through which gas is supplied to compensate for fluid withdrawn from the chamber in a manner which will be appreciated from ensuing description. As shown in FIG. 1, the nipple 32 has a break away sealing means 33. After the said sealing means 33 is removed, a hose 34 has one end secured thereto.

A nebulizer fitting or adapter generally designated 35 has a body 36 preferably of rigid plastic fabrication. A vertically orientable lower socket 38 is formed in said body with an internal spiral thread 40. The latter operably matches external thread 42 formed on duct 22, whereby the adapter may be mounted on container 10. An internally threaded upper socket 44 formed above socket 38 in body 36 for receiving the male component of oxygen supply means 26 adapts fitting 36 for connection to an oxygen pressure source.

Above socket 38 is an upper horizontally extending member 46 which terminates centrally with the bore of the socket 38 therebelow with an downwardly projecting cylindrical section 48 with a pocket 50. A breaching tool, generally, 52 has an upper tubular end 53 snugly seated in pocket 50. It has a lower breaching element 54 which is adapted for rupturing diaphragm 24 and projects into duct 22 when fitting 35 is operably associated with container 10. An axial vertical bore 56 for water projects through breaching tool 52.

The breaching tool has an outwardly radially projecting portion 57 intermediate tubular end 53 and the breaching element 54 which is approximately the same diameter as the internal diameter of the socket 38. An annular gasket 58 fits snugly against the underside of the projecting portion 57. The outer edge of the annular gasket 58 is threaded in a manner whereby it is screwed into the socket. The radially projecting portion 57 is held at its upper portion against a shoulder 59 of the socket by screwing the annular gasket 58 up against the underside of portion 57.

The tubular end 53 has a longitudinal axial slot 60 whereby the said end may be slightly compressed prior to being inserted into pocket 50.

Cylindrical section 48 terminates in an upper relatively flat top 61 having axially disposed a relatively small opening 62.

The upper socket 44 is rotably sealingly secured to body 36. The said upper socket 44 has a lower cylindrical extending portion 63 which extends into a secondary socket 64 within body 36 and is concentrically disposed with respect to said secondary socket. The bottom of socket 44 terminates with a fairly large orifice 65, but less than the internal diameter of the socket 44. The orifice 65 encompasses concentrically upwardly extending cylindrical projection 66 which has a bore 67 therethrough. The projection 66 and the bore is somewhat vertically displaced with respect to conduit 56 and cylindrical section 48. An annular member 68 is secured to the projection 66 and has a somewhat larger diameter. The larger dimension adapts it to overlie the uppermost portion of projection 66. The annular member 68 fits snugly against the internal side of socket 44. The downwardly extending underside abuts against the bottom of the socket 44. The annular member 68 retains the socket 44 in place but, as it is not affixed thereto, the socket is rotatable. By the assistance of ears 69 on the socket 44 the socket may be threaded onto the male member 26 of the oxygen supply means.

The venturi effect is produced by separate tubular venturi means 70 which fits into a bore 71 in a section 72 at the confluence of section 48 and projection 66. The venturi means 70 has a bore 74 therethrough with a restriction 73 intermediate the ends thereof. A downwardly radially extending bore 75, in the said restriction 73 provides a fluid communication between conduit 56 and the bore 74 of the venturi means 70.

Figure 7:
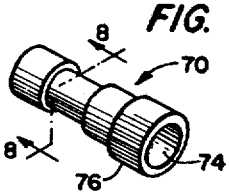
FIG. 7 is a perspective view of the venturi means of the present invention.
Figure 8:
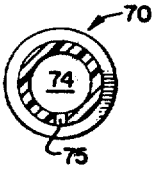
FIG. 8 is a cross-sectional view taken along line 8—8 of FIG. 7.
Figure 9:
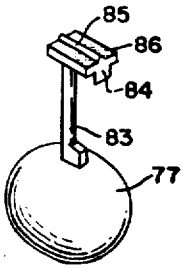
FIG. 9 is a perspective view of the baffle means employed in the present invention.

For an enlarged view of the venturi means 70, attention is directed to FIGS. 7 and 8. It will be noted that, especially from FIGS. 2 and 3 that what constitutes the downstream portion has a wider portion 76 which has an external somewhat larger than bore 71 and the external diameter of the remainder of the venturi means 70. The wider portion 76 acts as a flange to permit the venturi means 70 to be thrust into bore 71 only up to the beginning of the said wider portion 76. This arrangement assists in the assembly of the device as the bore 75 of the venturi means 70 is in proper alignment when the wider portion 76 and is in abutment with section 72.

The degree of delivery of the venturi means 70 depends in part on the diameter of the bore 75. By presizing the bore of a variety of venturi means it is possible to make available fittings 35 with a predetermined delivery.

The water is drawn up conduit 56 and is entrained with oxygen which is passed through bore 67 into the end of bore 74 and therethrough in the direction of ball 77 which acts as a further atomizer for the oxygen and water mixture. Droplets of water, not properly nebulized will form on the ball 77 and fall therefrom to the bottom inside of horizontally disposed tubular chamber 78. This chamber 78 will be seen to be perpendicular to the main body 36.

The chamber 78 has an opening 79 at the bottom thereof with a downwardly descending nipple 80 to which the other end of the water return line 34 is secured. To assist in collecting and leading the droplets of water to the opening 79 a ridge 81 is positioned along the bottom of chamber 78. This ridge 81 can be best seen from FIGS. 3 and 4. The ridge 81 extends over the bore 79. Downwardly depending therefrom is a relatively short projection 82 which assists in the formation of drops for return through water return conduit 34.

The ball 77 is suspended from the top of chamber 78 by means of downwardly depending spoke 83 which is secured to substantially one end of a small base 84. The base 84 has somewhat a T-shaped configuration with a ridge 85 at the top thereof. As the chamber 78 is cylindrical the base 84 will touch the inner surface of the chamber along the ridge 85 and the longitudinal side edges 86. The base is secured to the top of the chamber 78 by integral downwardly depending rails 87 which converge to hold the base 84 securely. The convergence feature provides ease for assembly.

Figure 6:
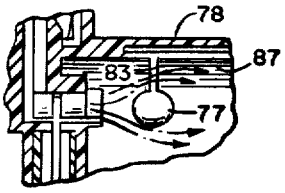
FIG. 6 is a fragmentary vertical sectional view of the device showing a different mode for a baffle means.

As the spoke 83 is attached to the base 84 at one end, it will be appreciated that when assembled, the ball 77 will be closer to the venturi means 70 when the base is facing in one direction than when it is facing in the opposite. In FIG. 2 the base 84 is secured in the chamber 78 with the spoke at the left side on that the ball is closest to the venturi means 70. From FIG. 6, it will be gleaned that the base 84 has been inserted between the rails 87 in an opposite manner. The result being that the ball 77 is not as close.

The device of the present invention is also supplied with means to provide for the addition of a controlled amount of filtered air. Accordingly, body 36 is provided with an orifice 90 at the side opposite to chamber 78. The orifice 90 is fitted with a filter medium 91 such as a foamed polyurethane disc. The degree of air entrainment is controlled by a slidably mounted arcuate plate 92 which is designed to monitor the effective aperture size with respect to the orifice 90, as seen from FIGS. 1–3. The plate 92 is easily moved by thumb projection 93 in a vertical manner. The air is drawn into chamber 94 which surrounds section 48, 66 and 72 and communicates with chamber 78.

In operation a 90° elbow 95 is provided and is secured to the open ended portion of chamber 78, as in FIG. 1. The other end of the elbow is secured to an elongated flexible conduit 96 which is directed towards the patient. It is important that the elbow 95 be secured so that the end secured to the conduit 96 is facing upwardly. In this manner the droplets of water in chamber 78 will be sure to run towards bore 79 eventually and no liquid water will run into the conduit 96 in the direction of the patient.

As many changes in the described construction could be conceived, and as many changes could be made therein without departing from the spirit and scope of the claims, it is intended that all matter contained in the specification shall be considered or illustrative only and not in a limiting sense.

What is claimed is:

1. A nebulizer adapted to be screwed onto a receptacle having an upwardly facing threaded portion adapted to receive the nebulizer, the receptacle being closed at said threaded portion by a breachable membrane, *said nebulizer* comprising a body having a hollow portion and downwardly facing socket, said socket being threaded whereby the nebulizer may be screwed onto the threaded portion of said receptacle, said socket having concentrically a breaching tubular means adapted for one end to breach said membrane, said body having a venturi means positioned in the hollow portion, the other end of said breaching tubular means being in fluid communication with a conduit terminating at the venturi transverse with the venturi means, a second socket means adapted to receive a connection means from a source of pressurized fluid, said second socket means being in fluid communication with the upstream portion of said venturi means, said body having a chamber means, the downstream portion of said venturi means terminating in said chamber means, said chamber means having a ball means disposed downstream of said venturi and displaced therefrom, whereby fluid emanating from said venturi impinges on said ball, said chamber means having an outlet at the bottom thereof for draining liquid, said chamber means having at the bottom an elongated axially disposed ridge, said hollow portion being at one side in fluid communication with said chamber means, and said body having an opening at substantially the other side thereof in communication with said hollow portion.

2. [The nebulizer of claim 1] *A nebulizer adapted to be screwed onto a receptacle having an upwardly facing threaded portion adapted to receive the nebulizer, the receptacle being closed at said threaded portion by a breachable membrane, said nebulizer comprising a body having a hollow portion and downwardly facing socket, said socket being threaded whereby the nebulizer may be screwed onto the threaded portion of said receptacle, said socket having concentrically a breaching tubular means adapted for one end to breach said membrane, said body having a venturi means positioned in the hollow portion, the other end of said breaching tubular means being in fluid communication with a conduit terminating at the venturi transverse with the venturi means, a second socket means adapted to receive a connection means from a source of pressurized fluid, said second socket means being in fluid communication with the upstream portion of said venturi means, said body having a chamber means, the downstream portion of said venturi means terminating in said chamber means, said chamber means having a ball means disposed downstream of said venturi and displaced therefrom, whereby fluid emanating from said venturi impinges on said ball, said chamber means having an outlet at the bottom thereof for draining liquid, said hollow portion being at one side in fluid communication with said chamber means, and said body having an opening at substantially the other side thereof in communication with said hollow portion,* wherein [the] *an* elongated axially disposed ridge bridges said outlet and has a member downwardly depending into said outlet from said bridging portion.

3. [The nebulizer of claim 1] *A nebulizer adapted to be screwed onto a receptacle having an upwardly facing threaded portion adapted to receive the nebulizer, the receptacle being closed at said threaded portion by a breachable membrane, said nebulizer comprising a body having a hollow portion and downwardly facing socket, said socket being threaded whereby the nebulizer may be screwed onto the threaded portion of said receptacle, said socket having concentrically a breaching tubular means adapted for one end to breach said membrane, said body having a venturi means positioned in the hollow portion, the other end of said breaching tubular means being in fluid communication with a conduit terminating at the venturi transverse with the venturi means, a second socket means adapted to receive a connection means from a source of pressurized fluid, said second socket means being in fluid communication with the upstream portion of said venturi means, said body having a chamber means, the downstream portion of said venturi means terminating in said chamber means, said chamber means having a ball means disposed downstream of said venturi and displaced therefrom, whereby fluid emanating from said venturi impinges on said ball, said chamber means having an outlet at the bottom thereof for draining liquid, said hollow portion being at one side in fluid communication with said chamber means, and said body having an opening at substantially the other side thereof in communication with said hollow portion,* wherein a filter is positioned in the opening at the side of the body opposite to the chamber means.

4. The nebulizer of claim 3 wherein the opening has a valve means to control the size thereof.

5. [The nebulizer of claim 1] *A nebulizer adapted to be screwed onto a receptacle having an upwardly facing threaded portion adapted to receive the nebulizer, the receptacle being closed at said threaded portion by a breachable membrane, said nebulizer comprising a body having a hollow portion and downwardly facing socket, said socket being threaded whereby the nebulizer may be screwed onto the threaded portion of said receptacle, said socket having concentrically a breaching tubular means adapted for one end to breach said membrane, said body having a venturi means positioned in the hollow portion, the other end of said breaching tubular means being in fluid communication with a conduit terminating at the venturi transverse with the venturi means, a second socket means adapted to receive a connection means from a source of pressurized fluid, said second socket means being in fluid communication with the upstream portion of said venturi means, said body having a chamber means, the downstream portion of said venturi means terminating in said chamber means, said chamber means having a ball means disposed downstream of said venturi and displaced therefrom, whereby fluid emanating from said venturi impinges on said ball, said chamber means having an outlet at the bottom thereof for draining liquid, said hollow portion being at one side in fluid communication with said chamber means, and said body having an opening at substantially the other side thereof in communication with said hollow portion,* wherein the said ball is secured to a base means and is suspended from an internal wall portion of said chamber means, said wall portion having converging rails adapted to receive said base means.

6. The nebulizer of claim 5 wherein the ball is secured to substantially one end of said base means.

7. The nebulizer of claim 1 wherein the breaching tubular means has a radially extending portion adapted to fit said downwardly facing socket to constitute the end thereof and to constitute the bottom of the hollow portion of said hollow body.

8. The nebulizer of claim 7 wherein the breaching tubular means is retained in position by a threaded annular member adapted to be screwed into said downwardly facing socket and to lie in abutment against the underside of said radially extending portion.

9. [The nebulizer of claim 1] *A nebulizer adapted to be screwed onto a receptacle having an upwardly facing threaded portion adapted to receive the nebulizer, the receptacle being closed at said threaded portion by a breachable membrane, said nebulizer comprising a body having a hollow portion and downwardly facing socket, said socket being threaded whereby the nebulizer may be screwed onto the threaded portion of said receptacle, said socket having concentrically a breaching tubular means adapted for one end to breach said membrane, said body having a venturi means positioned in the hollow portion, the other end of said breaching tubular means being in fluid communication with a conduit terminating at the venturi transverse with the venturi means, a second socket means adapted to receive a connection means from a source of pressurized fluid, said second socket means being in fluid communication with the upstream portion of said venturi means, said body having a chamber means, the downstream portion of said venturi means terminating in said chamber means, said chamber means having a ball means disposed downstream of said venturi and displaced therefrom, whereby fluid emanating from said venturi impinges on said ball, said chamber means having an outlet at the bottom thereof for draining liquid, said hollow portion being at one side in fluid communication with said chamber means, and said body having an opening at substantially the other side thereof in communication with said hollow portion,* wherein the said second socket means include an internally threaded rotatable portion.

10. [The nebulizer of claim 1] *A nebulizer adapted to be screwed onto a receptacle having an upwardly facing threaded portion adapted to receive the nebulizer, the receptacle being closed at said threaded portion by a breachable membrane, said nebulizer comprising a body having a hollow portion and downwardly facing socket, said socket being threaded whereby the nebulizer may be screwed onto the threaded portion of said receptacle, said socket having concentrically a breaching tubular means adapted for one end to breach said membrane, said body having a venturi means positioned in the hollow portion, the other end of said breaching tubular means being in fluid communication with a conduit terminating at the venturi transverse with the venturi means, a second socket means adapted to receive a connection means from a source of pressurized fluid, said second socket means being in fluid communication with the upstream portion of said venturi means, said body having a chamber means, the downstream portion of said venturi means terminating in said chamber means, said chamber means having a ball means disposed downstream of said venturi and displaced therefrom, whereby fluid emanating from said venturi impinges on said ball, said chamber means having an outlet at the bottom thereof for draining liquid, said hollow portion being at one side in fluid communication with said chamber means, and said body having an opening at substantially the other side thereof in communication with said hollow portion,* wherein the venturi means comprises a separate tubular means and said nebulizer has a bore in a block means in the hollow portion adapted to operatively accept said separate tubular means.

* * * * *